United States Patent
Sahu et al.

(10) Patent No.: US 9,880,144 B2
(45) Date of Patent: Jan. 30, 2018

(54) ELECTROCHEMICAL METAL AND ALLOY DETECTOR AND METHOD

(71) Applicant: Palo Alto Research Center Incorporated, Palo Alto, CA (US)

(72) Inventors: Saroj Sahu, Fremont, CA (US); Craig Eldershaw, Belmont, CA (US); Vedasri Vedharathinam, San Jose, CA (US); Divyaraj Desai, San Jose, CA (US); Jessica Louis Baker Rivest, Palo Alto, CA (US); Ranjeet Rao, Redwood City, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 367 days.

(21) Appl. No.: 14/576,309

(22) Filed: Dec. 19, 2014

(65) Prior Publication Data

US 2016/0178563 A1 Jun. 23, 2016

(51) Int. Cl.
*G01N 27/333* (2006.01)
*G01N 33/20* (2006.01)
*G01N 27/416* (2006.01)
*G01N 27/30* (2006.01)

(52) U.S. Cl.
CPC .......... *G01N 33/20* (2013.01); *G01N 27/416* (2013.01); *G01N 27/308* (2013.01)

(58) Field of Classification Search
CPC ...... G01N 27/26–27/28; G01N 27/283; G01N 27/286; G01N 27/70; G01N 27/4161; G01N 27/4166–27/4168; G01N 27/42–27/44; G01N 33/20; G01N 33/203; G01N 33/206

USPC .......... 204/194, 400–402, 404–423; 205/775.5–777, 790, 790.5–791.5
See application file for complete search history.

(56) References Cited

U.S. PATENT DOCUMENTS

| | | | |
|---|---|---|---|
| 4,190,501 A | 2/1980 | Riggs, Jr. | |
| 4,294,667 A | 10/1981 | Yamamoto | |
| 5,080,766 A * | 1/1992 | Moment | G01N 33/20 204/406 |
| 5,218,303 A * | 6/1993 | Medvinsky | G01N 27/416 205/790 |
| 5,425,869 A * | 6/1995 | Noding | G01N 27/4045 204/416 |
| 5,568,990 A | 10/1996 | McAuley | |
| 5,792,337 A | 8/1998 | Padovani | |
| 6,398,931 B1 | 6/2002 | Burchette et al. | |
| 7,695,601 B2 | 4/2010 | Jiang et al. | |
| 9,316,613 B2 | 4/2016 | Unwin et al. | |
| 2009/0014422 A1 | 1/2009 | Miklos | |

(Continued)

FOREIGN PATENT DOCUMENTS

EP  2063263 A2  5/2009
FR  1142731 A   9/1957

(Continued)

OTHER PUBLICATIONS

EP Search Report 16154251.9-1554 /3050591 dated Jul. 27, 2016.

(Continued)

*Primary Examiner* — Bach T Dinh
(74) *Attorney, Agent, or Firm* — Fay Sharpe LLP

(57) ABSTRACT

Disclosed is an electrochemical probe system and an electrical excitation method, used to identify the composition of metals and alloys.

19 Claims, 12 Drawing Sheets

(56) References Cited

U.S. PATENT DOCUMENTS

| | | | |
|---|---|---|---|
| 2009/0166198 A1* | 7/2009 | Du | G01N 27/301 204/416 |
| 2012/0285827 A1 | 11/2012 | Dunn | |
| 2013/0220807 A1* | 8/2013 | Radomyshelsky | G01N 33/20 204/406 |
| 2014/0096796 A1 | 4/2014 | Frum | |
| 2016/0245773 A1 | 8/2016 | Eldershaw | |
| 2016/0245775 A1 | 8/2016 | Eldershaw | |

FOREIGN PATENT DOCUMENTS

| | | |
|---|---|---|
| GB | 1334597 A | 10/1973 |
| WO | WO 2008/087687 A2 | 7/2008 |

OTHER PUBLICATIONS

EP Search Report 16154254.3-1554 dated Jul. 7, 2016.
A Abal Associacao Brasileira do Aluminio, retrieved from the Internet Dec. 16, 2014, http://www.abal.org.br/, 5 pgs.
Bruker Alloy Tester, Scrap Metal Identification & Sorting with Bruker XRF Scrap Guns, retrieved from the Internet Dec. 16, 2014, http://alloytester.com/scrap-metal-identification, 2 pgs.
Ashahi Kasei E-Materials Corporation, retrieved from the Internet Dec. 16, 2014, http://www.asahi-kasei.co.jp/hipore/en/index.html, 2 pgs.
Buckler, The ec-pen in quality control: Determining the corrosion resistance of stainless steel on-site, International Symposium (NDT-CE 2003), 5 pgs.
Huang, A Fast Two-Dimensional Median Filtering Algorithm, IEEE Transactions on Acoustics, Speech, and Signal Processing, vol. ASSP-27, No. 1, Feb. 1979, pp. 13-18.
Guthrie, Overview of X-ray Fluorescence, Archaeometry Laboratory, Univ. of Missouri Research Reactor, revised Aug. 2012, 9 pgs.
Celgard, Monolayer Polyethylene (PE), retrieved from the Internet Dec. 16, 2014, http://www.celgard.com/monolayer-pe.aspx, 1 pg.
Oxford Instruments, Optical Emission Spectroscopy (OES) for Metal Analysis, retrieved from the Internet Dec. 16, 2014, http://www.oxford-instruments.com/products/spectrometers/optical-emission-spectroscopy, 2 pgs.
Steel Recycling Instistute, Steel Recycling Information, News & Resources, retrieved from the Internet Dec. 16, 2014, http://www.recycle-steel.org, 2 pgs.
U.S. Environmental Protection Agency, Wastes-Resource Conservation—WARM, Wast Reduction Model (WARM), retrieved from the Internet Dec. 16, 2014, 2 pgs.
Freemantle, An Introduction to Ionic Liquids, 2010, published by the Royal Society of Chemistry, Introduction, Chapter 1, 10 pgs.
ARPA-E, Financial Assistance Funding Opportunity Announcement, U.S. Department of Energy, Modern Electro/Thermochemical Advances in Light-Metal Ssytems (Metals), Mar. 20, 2013, 84 pgs.
Median Filtr, Wikipedia, retrieved from the Internet Dec. 16, 2014, http://en.wikipedia.org/wiki/median_filtr, 1 pg.
PARSE: Developing the Future of U.S. Recycling, PARC Blog, Mar. 13-14, 2014, http://blogs.parc.com/blog/2014/02/parse-developing-the-future-of-u-s-recycling/, 2 pgs.
Scrap Specifications Circular 2013, Guidelines for Metals Transactions, Institute of Scrap Recycling Industries, Jul. 24, 2013, 6 pgs.
ASM Specialty Handbook, Aluminum and Aluminum Alloys, Edited by J.R. Davis, Dec. 1993.

* cited by examiner

ELECTROCHEMICAL METAL AND ALLOY DETECTOR AND METHOD

STATEMENT REGARDING FEDERALLY SPONSORED RESEARCH OR DEVELOPMENT

This invention was made with United States Government support under U.S. Department of Energy Cooperative Agreement No. DE-AR0000405 ARPAE-METALS-PARSE, beginning on Feb. 3, 2014 awarded by the U.S. Department of Energy. The United States Government has certain rights in the Invention.

TECHNICAL FIELD

The present disclosure relates generally to the field of metal and metal alloy identification, and more particularly to electrochemical systems and methods of identifying and separating metals and alloys.

BACKGROUND

Extracting metals from their ores is an energy intensive process. After extraction, the metals are commonly alloyed in different proportions to achieve certain physical or chemical characteristics. When the useful life of objects using these metals and alloys is over, they are typically sent to scrap yards and shredded to smaller pieces to be sold as aggregated scrap metals. Value of such aggregates is much lower compared to the fresh alloys, since they cannot be simply re-melted and re-used, due to their unknown composition. While lab methods such as atomic emission spectroscopy can identify each sample, the time taken for testing each sample may be several minutes, and requires sophisticated and expensive analytical tools. Therefore the cost of identification far outstrips the residual value of the scrap metal itself.

A large industry segment in the scrap materials business makes and uses machines that broadly separate some of the scrap components very fast, in matter of seconds. For instance, air-vortex separators remove plastics; Eddy-current separators remove glasses and plastics; Magnetic separators remove ferrous items; and X-ray assisted conveyor belts remove high atomic weight metals such as copper. However, within the same metal families, identifying and separating different alloys at a fast speed of seconds or less has been a challenge.

Several hand-held and portable instruments and technologies exist today that are capable of identifying different alloys, but they have not been integrated to high throughput conveyor-belt systems due to their slower speeds of 30 seconds to several minutes per test. Such technologies include: (a) X-ray fluorescence spectroscopy and (b) Laser-ablation spectroscopy, and variations and combinations of these. In X-ray spectroscopy, an X-ray beam excites the orbital electrons of the surface of the scrap sample, resulting in optical fluorescence. The fluorescence spectrum is measured by sensitive photo-detectors. Each metal has a characteristic spectrum, and by de-convoluting the spectrum, the metal components in the alloy can be determined. In Laser-ablation method, a very high power laser beam vaporizes a small amount of the surface of the sample, and an optical emission or absorption spectroscopy is done on the vapor to determine its composition. Both these technologies require 10-40 seconds to measure each sample, and cost between US$ 20,000 and US$ 40,000, making it prohibitive for implementation in conveyor-belt sorters. For such sorters, the identification must be made within a few seconds.

BRIEF DESCRIPTION

Provided are probing methods and systems for electrochemical identification of different metals and alloys.

Also provided is a set of electrochemical media that the probes could use that would identify different metals and alloys.

Still further, provided is a reliable electrochemical excitation, measurement and analytical method for identification of metals and alloys.

DETAILED DESCRIPTION

Two dissimilar conductors, such as metals or graphite, when separated by an electrolyte, which is not an electron conductor but an ionic conductor, will produce an electrochemical potential characteristic of the pair. This phenomenon is known, and theoretically can be used to identify different pure metals.

Figure 1:
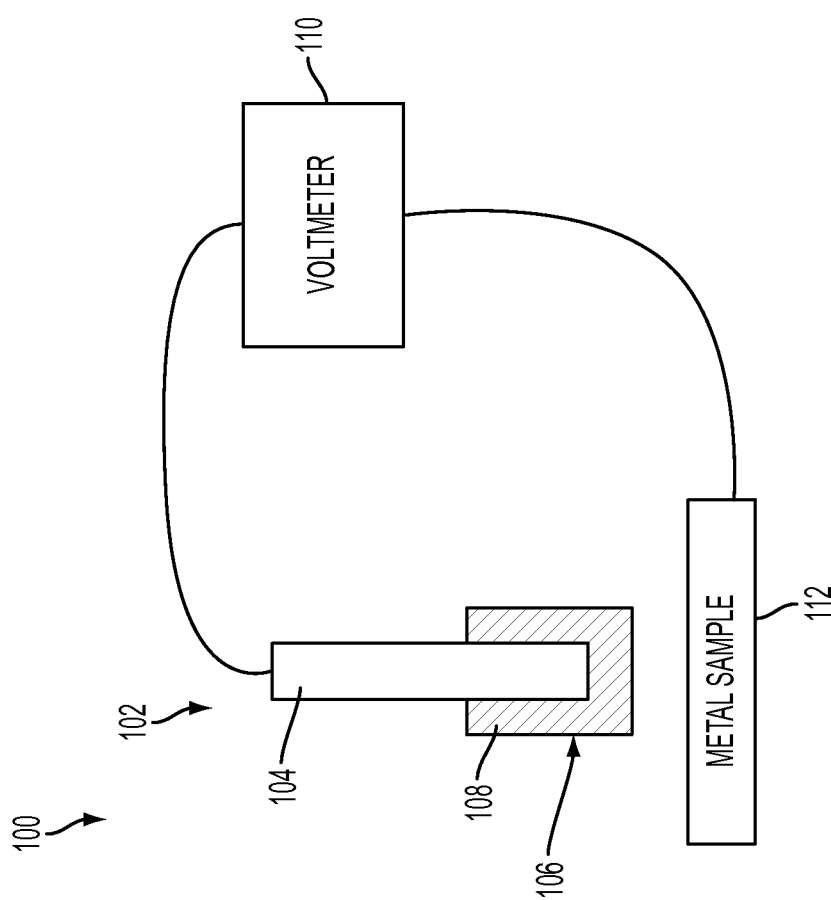
FIG. 1 is a drawing showing an electrochemical probe system described in the literature.

Such an arrangement 100 is shown in FIG. 1. The test system 102 of arrangement 100 includes a current collector probe 104, made out of glassy carbon, wrapped with a porous membrane 106 containing an electrolyte 108, such as 1-methyl-1-butyl-imidazolium-triflate, and an electrical measurement device 110, which in this embodiment may be a voltmeter. In operation probe 104 with membrane 106, is brought in contact with a sample 112, which is a particular type of metal, whereby the membrane 106 with electrolyte 108 is located there between. In this arrangement a potential is developed, called Open Circuit Voltage (OCV). The developed OCV is measured by the electrical measurement device 110. If the metal, electrolyte and probe are very pure in their composition, then the potential developed is characteristic of the metal being tested.

Figure 2:
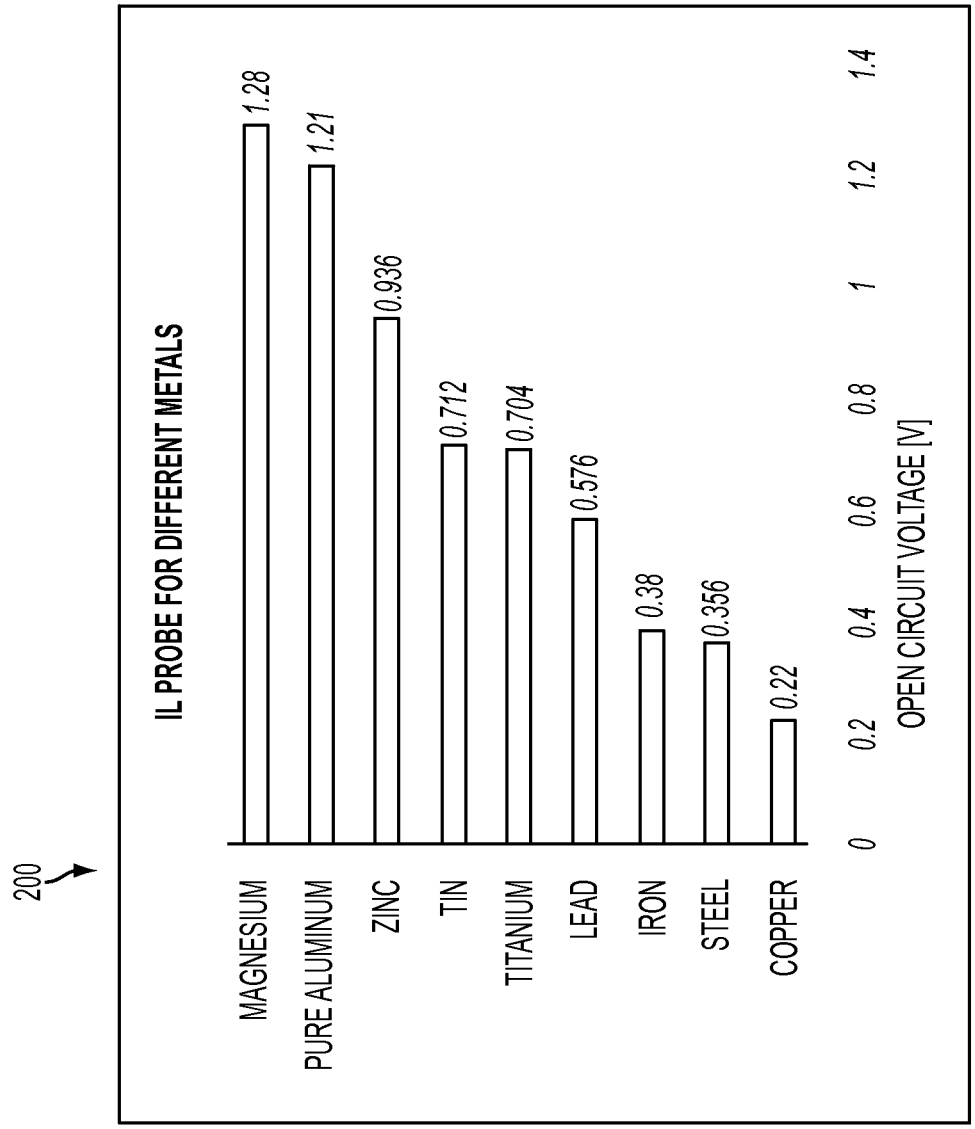
FIG. 2 is a plot showing measurement of OCVs for different metals using the electrochemical probe system of FIG. 1.

Using the arrangement 100 in FIG. 1 several metals have been tested and plotted as shown in FIG. 2. It may be seen that a variety of metals can be identified with this system and method. A technique as discussed above has been discussed in the literature. One problem with test system 102 is that even a very small amount of alloy component or impurity on the metal sample 112 or impurity in the electrolyte 108 changes the OCV dramatically. Additionally, another shortcoming is that OCV values drift over the time of measurement depending on different environmental or component conditions. Such issues make the system and method of FIG. 1 unreliable.

Turning more particularly to the presently disclosed system and method two aspects are initially mentioned:
1) Electrolytes (e.g., wafer-based electrolytes) that are capable of a reversible redox reaction with the metal and its alloy components are employed. It is noted that a cation of the electrolyte consists of a metal ion having at least two redox states that are soluble in the electrolyte medium.
2) An asymmetrical excitation charges and discharges the redox reaction rapidly and in such a manner that the net amount of electric charge (Coulombs) transacted to a sample is zero.

Figure 3:
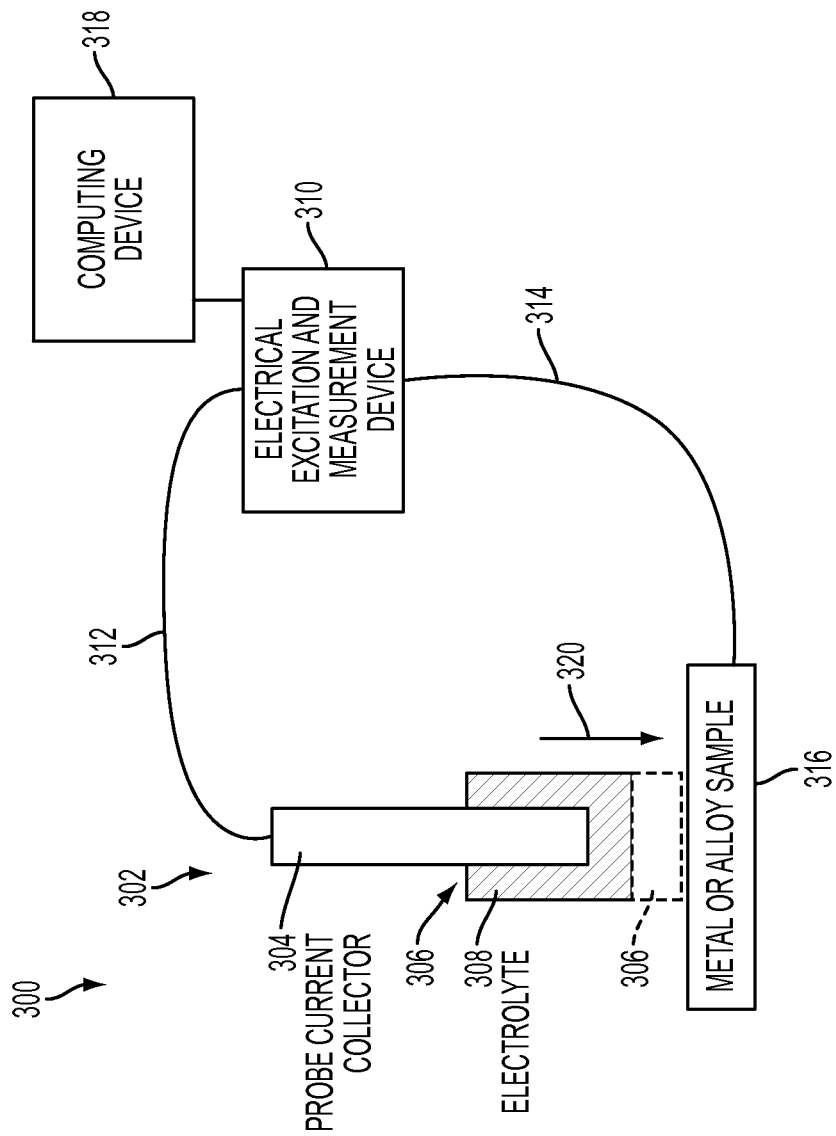
FIG. 3 illustrates an electrochemical probe based testing system according to the present application.

An arrangement 300 for testing samples consisting of different metals and metal alloys according to the teachings of the present application is shown in FIG. 3.

A testing system 302 of arrangement 300 includes a current collector probe 304, with a non-electrical conductive component (such as a membrane) 306 containing an electrolyte 308, and an electrical excitation and measurement device 310. The testing system further includes an electrical connection line 312 in operative electrical connection with the probe 304 and the electrical excitation and measurement device 310, and an electrical connection line 314 at one end in operative electrical connection to the electrical excitation and measurement device 310. The other end of electrical connection line 314 is positioned to be in operative electrical connection with sample 316 which is to be tested. Also provided as part of the test system 302 is a computing device 318 to record and/or store measured values (voltage and/or current) measured by the measurement portion of electrical device 310, and to perform operations to look-up or otherwise calculate and/or associate the recorded and/or stored measured values with previously known values that are characteristics of specific metals and/or metal alloys.

The probe 304 is formed of an appropriate material including but not limited to glassy carbon, graphite, carbon-plastic composite, other forms of carbon, a various metals, including, metal oxides, a metal salts or metal salt composites (e.g., Tin, Lead, and Indium) that form galvanic coupling through the electrolyte with the sample 316. The probe 304 may also be made from other materials including but not limited to chalcogenide. The membrane 306 is in certain embodiments a porous or fibrous polymeric material with open pores. In other embodiments the membrane is a non-porous ion exchange membrane. The membrane is, in certain embodiments configured in, but not limited to, a planar form, such as to cover just the bottom surface of the probe, while in other embodiments the membrane is formed as a sleeve with a bottom surface (e.g., a "cup" shape) that covers the end portion of probe 304 and well as a certain amount of the sides of the probe. Still further, in other embodiments the membrane is replaced with a meniscus as the component located between the probe 304 and the sample 316.

Arrow 320 of FIG. 3 indicates the movement direction of the probe 304 for operative contact between the probe 304, membrane 306 (with electrolyte 308), and sample 316, whereby an ionic path is formed. The operational contact being shown by dotted line connection to "306". In other embodiments it is the sample that is moved to the probe, and in still further embodiments both the probe and the sample are moved to make contact The movements being made by use of known technology. Measurements are capable of being made by the electronic device 310, with or without excitations from the electronic device 310 during the measurement operation.

Figure 4:
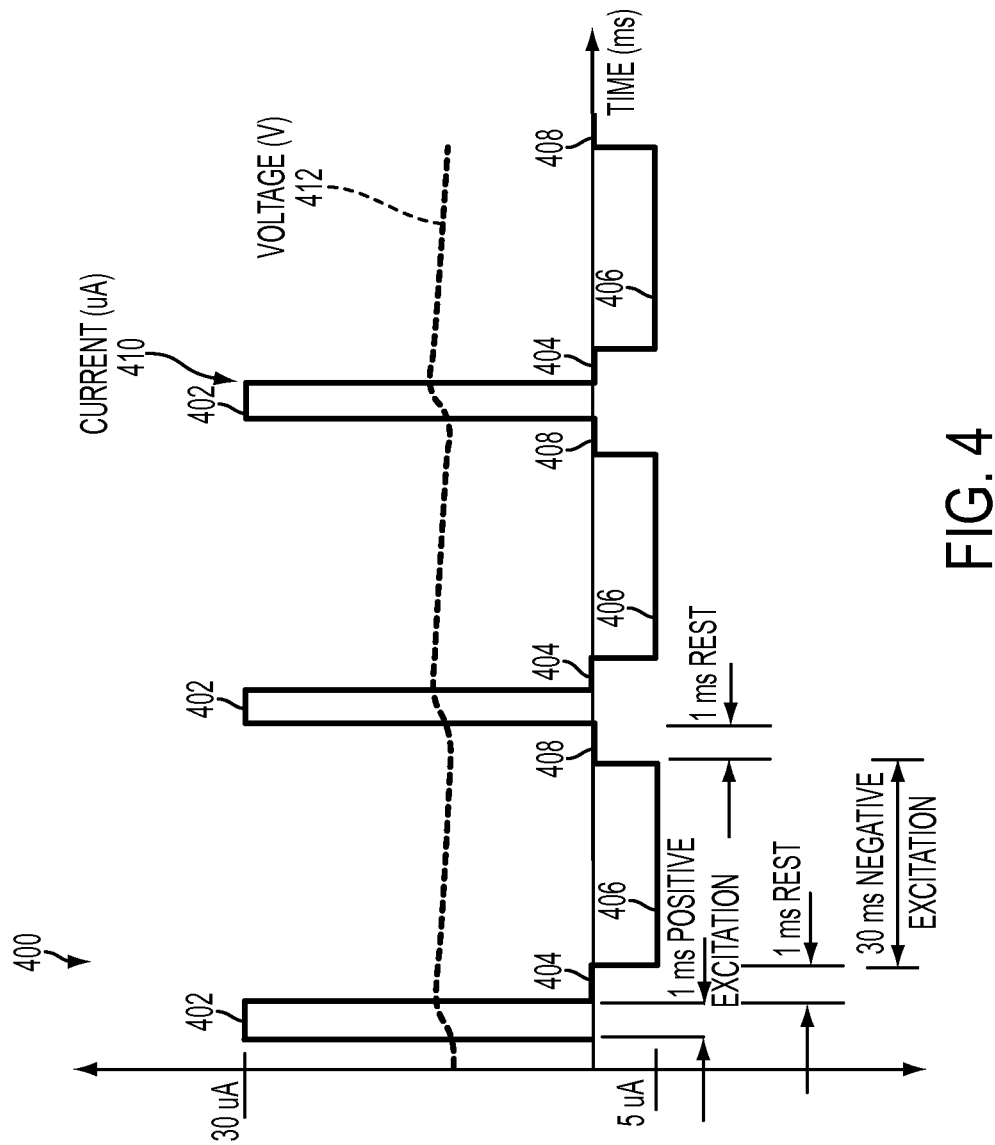
FIG. 4 is a plot showing asymmetric current excitation and resulting voltage response for the test system of FIG. 3.

Turning now to FIG. 4, excitations generated by the excitation portion of the electrical excitation and measurement device 310 of FIG. 3 is described in graph 400. In this disclosed embodiment, the described excitation sequence is followed—
I. Positive current of 30 uA for 1 mSec from probe into the sample metal/metal alloy (402).
II. Zero current (rest time) for 1 mSec (404).
III. Negative current of 5 uA for 30 mSec from metal into the probe (406).
IV. Zero current (rest time) for 1 mSec (408).
In this embodiment this sequence is repeated for 10 times (shown repeated three times in FIG. 4), and the output may then be averaged.

The plot of the value of the current as a function of time is shown by solid line 410.

While this sequence is running, the potential is measured via electrical device 310 of FIG. 3 as a function of time and recorded. The plot of the potential as a function of time is shown as the dotted line 412.

The pulse sequence of FIG. 4 is now explained in more detail. Technically, when one metal is brought into electrolytic contact with another metal, or more generally, when a conductor electrolytic and another conductor are brought into contact, there is no electron transfer, but there is ionic transfer, and a potential will exist. This potential is used to represent characteristics of the two metals. However, if there is no significant current being generated, a small amount of impurity in the system substantially changes the output being observed. For example if there is pure aluminum on one side, and pure graphite on the other side, but there is even a speck of impurity (such as iron), since there is no significant current flow, the iron acts to destabilize the output readings, meaning the sample metals cannot be reliably identified.

To address this issue, as shown in FIG. 4, current based cycle pulsing is provided for generating charging and discharging operations (which means the cycle pulsing is acting as a battery). Therefore, the relative magnitude of the metals or the composition of the metals is far more important than the impurities (e.g., the speck of iron). So impurities on the sample (e.g., aluminum) have a negligible effect on the testing operations (e.g., the voltages that are observed).

One reason the excitations being used are asymmetric is that (as in most batteries), charging is much more efficient than discharging. So the charging pulse is able to use a narrow pulse for a short time to achieve the desired results. The discharging cycle pulsing is selected with a current and time so that substantially the same number of electrons is extracted from the sample that were added during the charging operation. Discharging is normally slower than charging. Therefore more time is given to complete the discharge of the electrons, which again will result in substantially a net zero electron exchange (e.g., no net electrons are input to the sample) during one full pulsing cycle of FIG. 4.

A second reason the charging time is held short is to avoid the charging operation from generating a gas discharge, which could occur in some implementations with an extended charging time period.

The described pulsing sequence minimizes the impact of impurities on the sample being tested, by providing a current flow, while at the same time ensuring that a net zero exchange of electrons occur.

In the embodiment shown in FIG. 4, three full pulsing cycles (402-408) are depicted, each having: a charging period of one millisecond (402), a first rest period of one millisecond (404), a discharge period of 30 milliseconds (406), and a second rest period of one millisecond (408). For a total cycle of 33 milliseconds.

It is to be appreciated, these time periods and pulsing values are for a particular embodiment, and there can be applications where different time periods and values are to be used. In other embodiments, the charging operation may be anywhere in the range from 0.5 milliseconds up to 5 seconds. Similarly, the discharge may be anywhere in the range from 3 milliseconds to 30 seconds, and the rest periods from 0.5 milliseconds to 5 seconds. The actual selected time periods may be any within these selected ranges in accordance with a particular application. Additionally, current values may also vary dependent upon particular implementations of the system, such as anywhere in the range of 3 uA to 300 uA for the positive charging pulse and −0.5 uA to −50 uA for the discharging pulse, as long as the concept of having a substantially no net electron transfer once the entire pulsing cycle has been completed is maintained.

Further, while the discussion in connection with FIG. 4 indicted the use of ten cycles of each pulsing sequence (402-408), dependent upon the implementation as little as one pulsing cycle may in some embodiments be useful and in others, two or more pulsing cycles may be appropriate for the particular implementation.

It is noted however, that when large values are used, for example if five-second charge and 30-second discharge sequences are used the voltage swings will become larger, since as charging is taking place the voltage goes up, and as discharging, is occurring the voltage goes down, so having a longer duration in terms of charging and discharging, then the pulsing cycle (in the form of the saw-tooth waveform) would be fairly wide. Whereas, in the case of the 1 millisecond and 30 millisecond situation, the voltage line 412 is substantially flat, as shown in FIG. 4, which improves the ability to ensure substantially no net gain of electrons on either side. The present embodiments are using a charge balance technique.

Also, an aspect of the present disclosure is the speed at which the readings can be taken by the electronic device 310 of FIG. 3. Thus, the narrower the pulse width in the saw tooth wave arrangements, the faster the readings can be obtained. Thus using the values of FIG. 4, a testing operation to determine the identity of a specific sample would be:

1 Msec+1 Msec+30 Msec+1 Msec=33 Msec×10 cycles=330 Msec

Turning to a particular implementation, the inherent chemical reaction in the ionic process by a system such as system 300 of FIG. 3, in the case of using Ferric Chloride electrolyte for a Copper (Cu) sample can be written as follows—

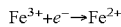
$$Fe^{3+}+e^-\rightarrow Fe^{2+}$$

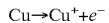
$$Cu\rightarrow Cu^++e^-$$

Cu, for instance, is the major alloy component for the 2xxx series of aluminum alloy. The amount of copper will therefore determine the average potential observed during the excitation.

Although copper is shown here as an example of the redox reaction, other metals undergo similar redox reactions and may therefore be identified with empirically determined voltage values.

Also, while this disclosure focuses it examples on identification of different aluminum alloys, other metals and metal-alloy systems, such as steel, bronze and gold systems can be identified with this method by an appropriate choice of electrolytes.

Figure 5:
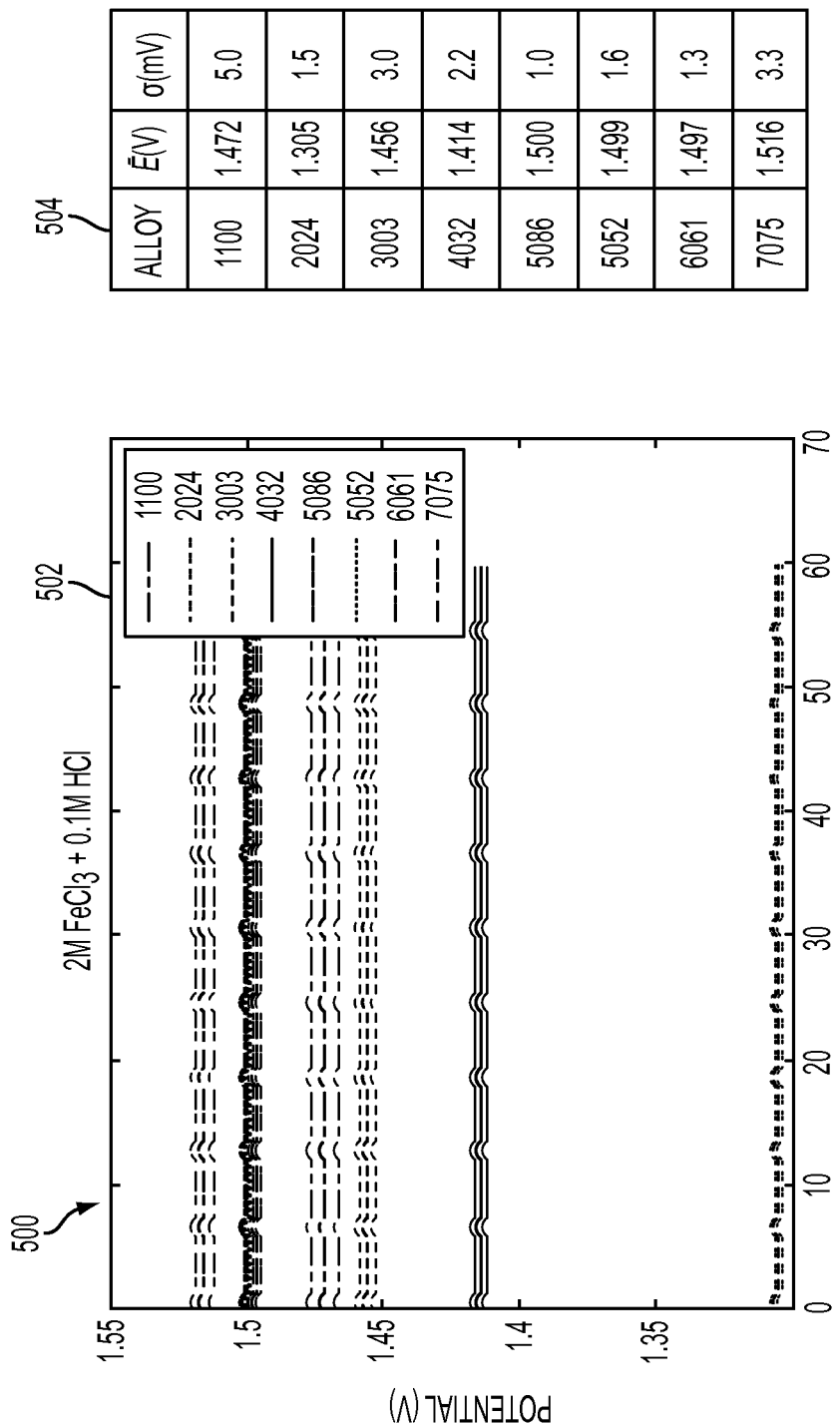
FIG. 5 is a plot graph and table showing measurement of voltage as a function of time with asymmetric alternating current excitation using Ferric Chloride electrolyte for different aluminum alloy compositions.
Figure 6:
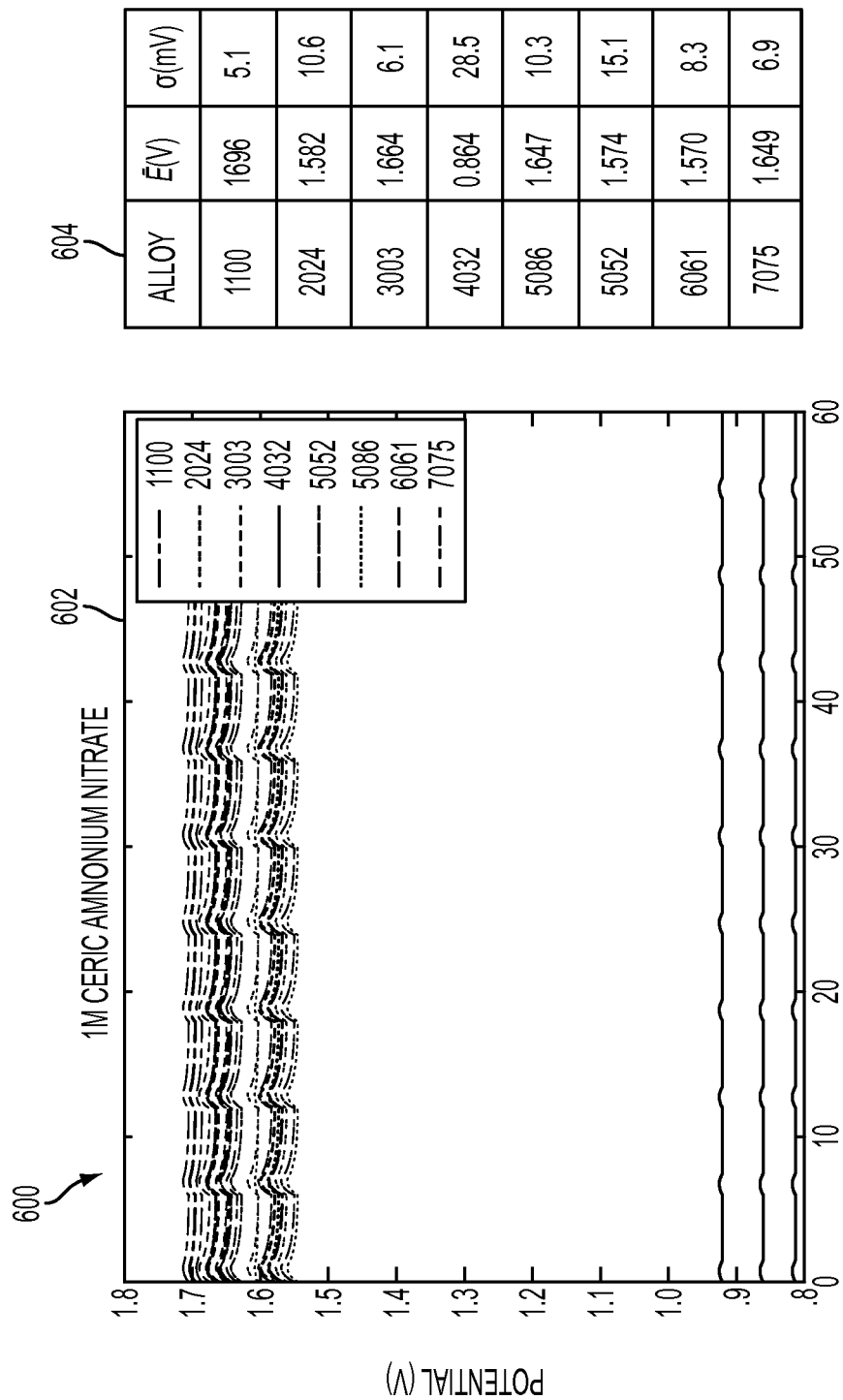
FIG. 6 is a plot graph and table showing measurement of voltage as a function of time with asymmetric alternating current excitation using Cerium Ammonium Nitrate for different aluminum alloy compositions.
Figure 7:
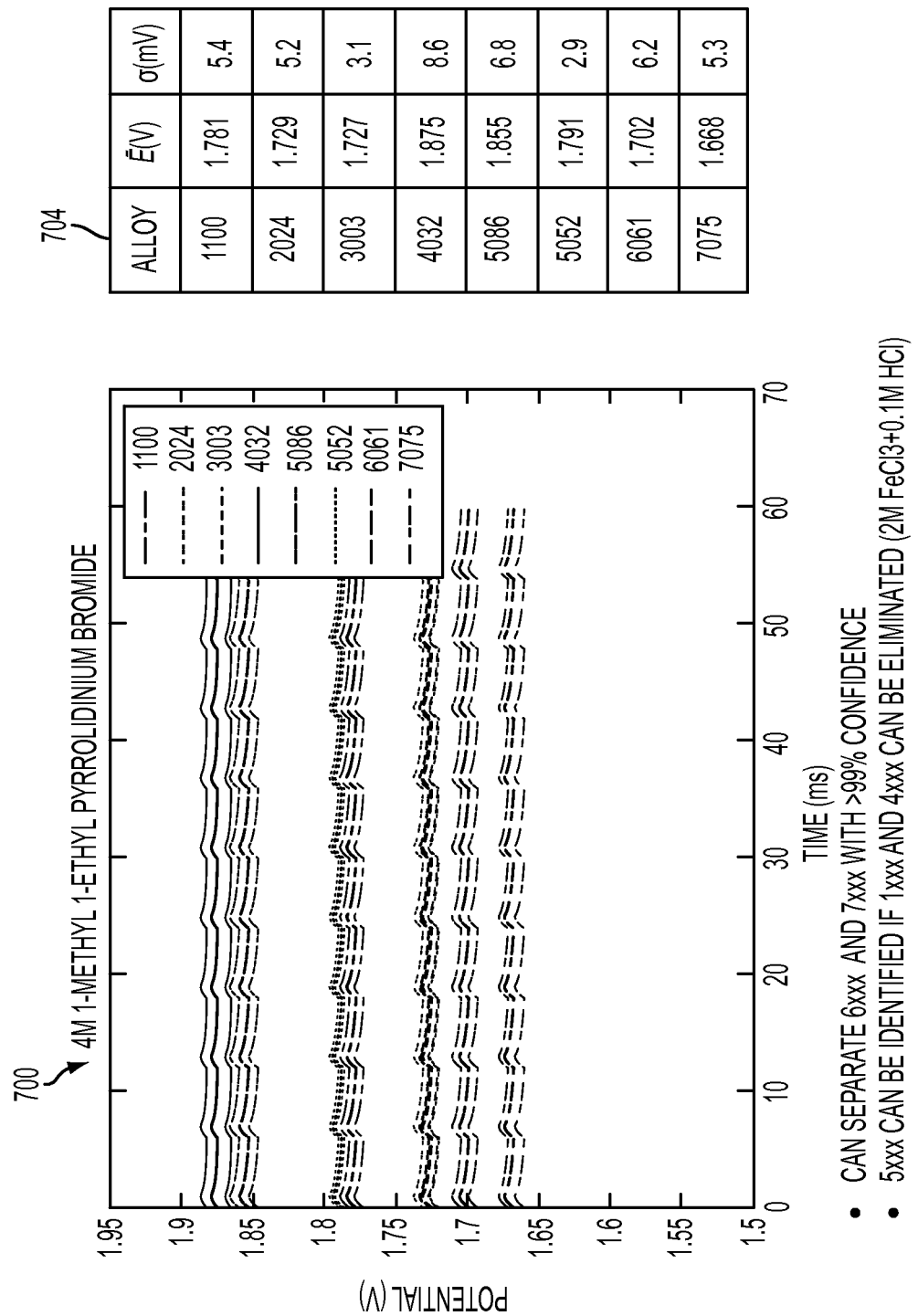
FIG. 7 is a plot graph and table showing measurement of voltage as a function of time with asymmetric alternating current excitation using 1-methyl 1-ethyl pyrrolidinium bromide electrolyte for different aluminum alloy compositions.

Using a testing system based on the teachings of FIG. 3, attention is now directed to results of testing operations as illustrated in FIGS. 5, 6 and 7.

Turning now to FIG. 5, the potential observed as a function of time for a Ferric-Ferrous system using Ferric Chloride electrolyte, for different Aluminum alloys is shown in illustrations 500, including graph plot 502 and corresponding table 504. It may be observed that while alloys 2024, 4032, 7075, and 3003 are clearly identified with widely separated voltages, alloys 5086 and 5052 are substantially indistinguishable from each other. However, the family of 5xxx alloys is distinguished from other alloys of table 504.

The above observations are shown in both plot graph 502 and table 504. More particularly, with attention to table 504, in the left-most column are the particular metal alloys being tested (1100, 2024, 3003, 4032, 5086, 5052, 6061 and 7075). The middle column lists the voltage readings (E (V)) for corresponding identified metal alloys, and the right most column lists the related sigma (σ) value (i.e., standard deviation values) of the test results for each of the noted alloys. More particularly, the sigma value represents the accuracy of the measured voltage values for corresponding samples. For example, when the standard deviation (σ) is 3.0 or greater (i.e., 3.0σ) the accuracy of the identification is greater than 99%. For 2.0σ or greater the accuracy of the test results is understood to be approximately 92% accurate. On the other hand, test results for alloys 5086, 5052, and 6061 of table 504 were found to be substantially indistinguishable from each other having a sigma (σ) of less than 2 and are, therefore considered not reliable.

It is considered that a testing system using a same electrolyte may not be able to distinguish all the alloys or metals in a given family, depending on the metal or alloy under investigation. In that case, a different electrolyte with the same excitation method would provide a different set of voltages, thus providing an orthogonal set of measurements.

For instance, illustrations 600 of FIG. 6, including a graph plot 602 and table 604 show test voltage results for different aluminum alloys for a testing system using a ceric ammonium nitrate electrolyte. Cerium has two redox states: +3 and +4. The correspondent reaction may then be—

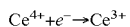
$$Ce^{4+}+e^-\rightarrow Ce^{3+}$$

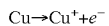
$$Cu\rightarrow Cu^++e^-$$

As can be observed, using this electrolyte, and the same testing system and excitation method shown in FIGS. 3 and 4, it is possible to separate the 4xxx aluminum alloy family quite well.

In another instance, the electrolyte used is 1-methyl-1-ethyl pyrrolidinium bromide (MEP Br). In this case, the redox reaction is—

$$Br^- \rightarrow Br + e^-$$

$$Cu^+ + e^- \rightarrow Cu$$

This electrolyte is sensitive to the surface oxides of the metals and alloys. Table 604 of FIG. 6 illustrate, as reflected in the sigma (σ) column of table 604 that only 4xxx series alloys have sigma (σ) values that have a 2σ or greater Turning now to FIG. 7 illustrations 700 include a graph plot 702 and table 704 of voltages for different aluminum alloys with 1-methyl-1-ethyl pyrrolidinium bromide (4M MEP Br) USED as the electrolyte. Similar to FIGS. 5 and 6, table 704 includes the voltages (E(V)) and the σ values (mV), for a number of alloy metal groups. In table 704 it is illustrated that the testing results of the present system are able to separate 6xxx and 7xxx with over 99% confidence (i.e., 3.0σ or greater). Whereas the alloy group 5xxx can be identified if 1xxx and 4xxx are eliminated (2M FeCl$_3$+0.1M HCl).

Figure 8:
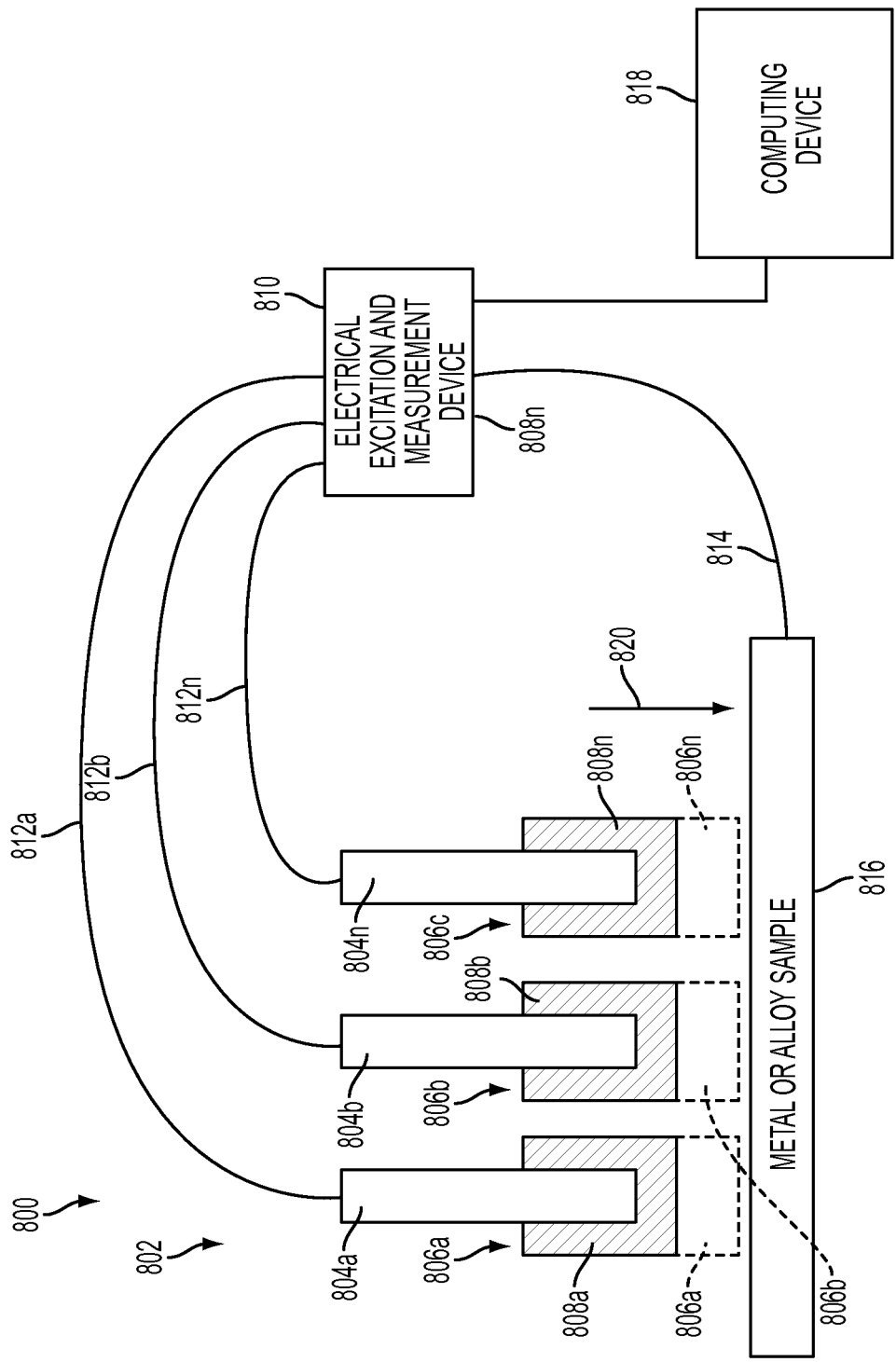
FIG. 8 illustrates an electrochemical probe based testing system according to the present application.

Turning now to FIG. 8, depending on the samples and range of identification and accuracy required, one or multiple electrolytes may be used in the identification problem. In FIG. 8, depicted is a multi-probe test system 802, having multiple current collection probes 804a, 804b, 804n and corresponding non-electrical conducting components (e.g., membranes) 806a, 806b, 806n with different suitable electrolytes 808a, 808b, 808n. that can probe a piece of metal at the same time or in sequence, and/or probe different samples in parallel. Test system 802 further includes an electrical excitation and measurement device 810 (such as electrical device 310 shown in FIG. 3), electrical connection lines 812a, 812b, 812n in operative connection with corresponding probes 804a, 804b, 804n and the electrical excitation and measurement device 810, and an electrical connection line 814 extending and in operative contact to the electrical excitation and measurement device 810 at one end. The other end of electrical connection line 814 is in operational electrical contact with the sample 816 to be tested. Also provided as part of the testing system 802 is a computing device 818 to record the values measured by the measurement portion of electrical device 810, and to perform operations to look-up or otherwise calculate and/or associate the recorded measured values with pre-determined values that are associated with specific metals and or metal alloys, such as shown in FIGS. 5, 6, 7.

A look-up table, stored for example on computing device may be used to classify the alloy or metal into different categories. The look-up table is established empirically by measuring known reference metal and/or metal alloy compositions. The computing device 818 (and 318 of FIG. 3) in certain embodiments is a computer, laptop, electronic pad, handheld or other smart electronic devices. In other embodiments the computing device is an electronic device dedicated to the present operations. The computing device includes a memory for storing software and/or a lookup table to perform operations to correlate the detected voltage and/or current values to empirically determined voltages that represent specific metals and/or metal alloys.

As similarly illustrated in FIG. 3, an arrow 820 shows a movement direction of probe 804 which provides operational contact between the probe 804, membrane 806 (with electrolyte 808), and sample 816, by which an ionic path is formed. The operational contact being represented by dotted connection lines for "306a", "306b" and "306n". In other embodiments it is the sample 816 that may be moved to the probe, and in still further embodiments, both probe and sample are moved to make contact. The movements being accomplished by known control technology.

The probe and non-electrically conductive component arrangements of FIG. 8 may be used to individually probe different samples sequentially and/or in parallel. Alternatively, more than a single probe may be used to probe the same sample. The probe/non-electrically conductive component arrangements may use the same electrolyte, or different electrolytes for different ones of the probe/non-electrically conductive component arrangements. For example, when the more than a single arrangement is used to test the same sample each arrangement may have a different electrolyte. Using different electrolytes, will for certain implementations, provide a more detailed and/or reliable identification of the sample.

Figure 9:
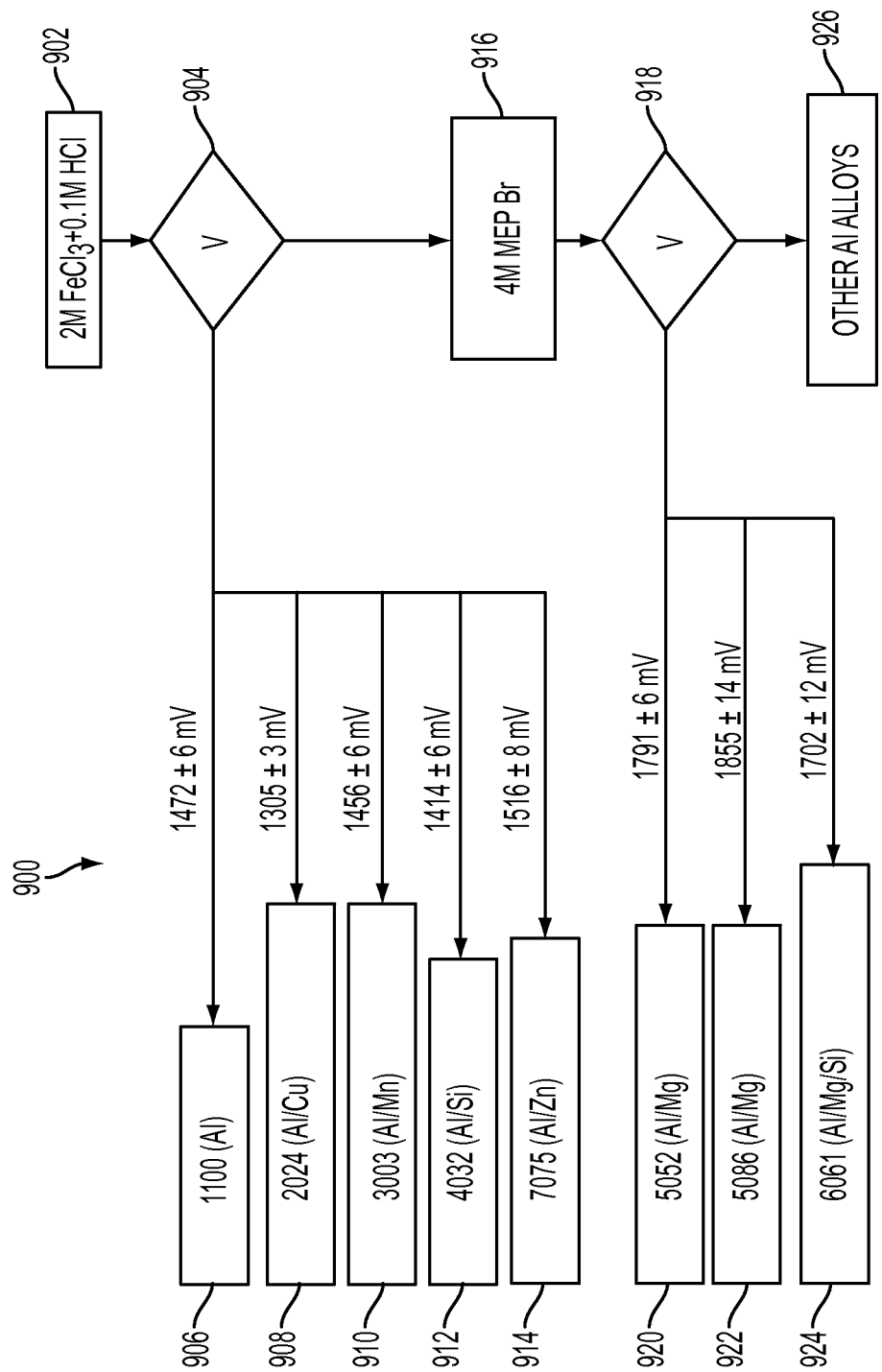
FIG. 9 is a flow chart algorithm to identify different aluminum alloys using asymmetric current excitation and two probes using two different redox electrolytes.

Turning to FIG. 9, depicted is a flow chart 900, which may be used to generate an algorithm (software) for use with computing device 818, for identifying/separating a variety of aluminum alloys using two different electrolytes for different probe/non-electrically conductive component arrangements. FIG. 9 represents a flow chart for 95% accurate sorting of aluminum alloys. Accordingly, the ranges are reported as ±2σ value. Initially, a first electrolyte (2M FeCl$_3$+0.1M HCl) at block 902 is used in electrochemical test system (e.g., 802 such as described in FIG. 8). In initial testing (block 904) the electrolyte of block 902 is used in the testing of samples identified by blocks 906, 908, 901, 912, and 914. Where the samples are unidentified at the time of testing. The millivolt potentials (1472+/−10 mV, 1305+/−3 mV, 1456+/−6 mV, 1414+/−6 mV, 1516+/−8 mV) that are obtained for the respective samples (boxes 906-914) are correlated to previously identified voltages that are characteristic of corresponding metals/metal alloys (in this example aluminum/aluminum alloys), including aluminum and aluminum alloy groups 1100, 2024, 3003, 4032, 7075.

The previously mentioned characteristic voltages, in one instance are found by empirical observation of known metals/metal alloys. These characteristic voltages are sorted in a look-up table, or used as part of an algorithm, or in other manners that allow for a matching of the measured voltage value(s) to the known characteristic voltage value(s), such as in a computing device described in FIG. 8.

FIG. 9 includes a second electrolyte (4M MEP Br) used with a separate probe/non-electrically conductive component arrangement (block 916). In initial testing employing these systems the second electrolyte is used to obtain voltage(s) as designated by diamond (V) 918 for a plurality of metallic samples. The obtained voltages 1791+/−6 mV, 1855+/−14 mV, 1702+/−12 mV, are again correlated to specific aluminum and/or aluminum alloys 5052, 5086, 6061, shown by blocks 920, 922, and 924 respectively. Block 926 acknowledges that the systems described herein may be used with other electrolytes to identify additional metals/metal alloys.

Figure 10:
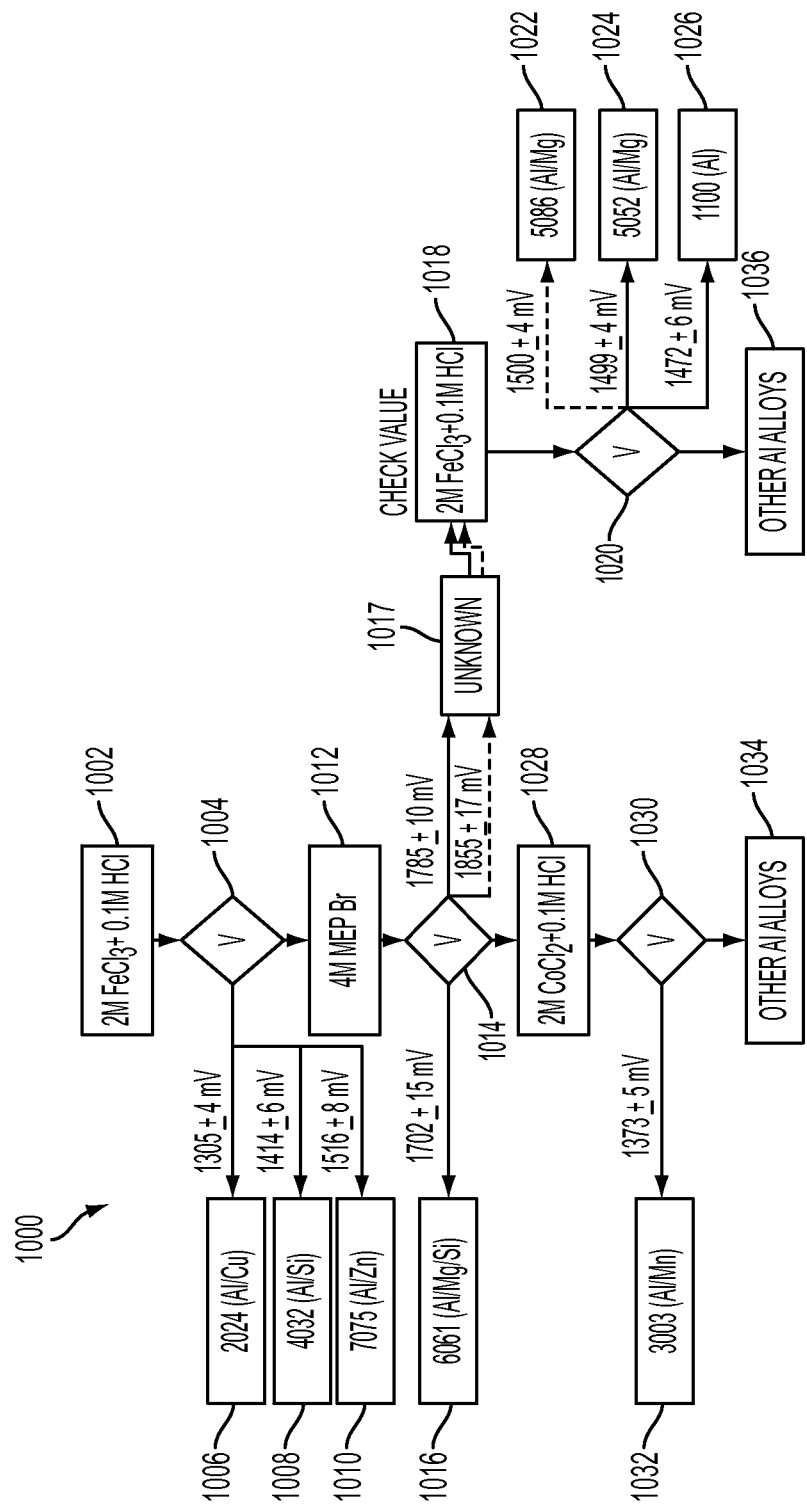
FIG. 10 is a flow chart algorithm to identify different aluminum alloys using asymmetric current excitation and three probes using three different electrolytes.

Shown in FIG. 10 is a flow chart 1000 for separating a variety of aluminum alloys based on a look up table or other correlation mechanism, using three electrolytes.

Initially, an electrolyte (2M FeCl$_3$ 0.1M HCl) in box 1002 is used in a test system, such as test system 802 of FIG. 8, where the testing operation "V" (diamond 1004) is used to test samples 1006, 1008, 1010, the metallic content of which is not known at the time of testing. The testing operation 1004, results in the generation of specific millivolt potentials (respectively, 1305+/−4 mV, 1414+/−6 mV, and 1516+/−8 mV). These measured values are then correlated to voltages values that are known to be characteristic of specific metal compositions (e.g., 2024 (Al/Cu), 4032 (Al/Si), 7075 (Al/Zn)). Thus the testing operation identifies previously unidentified metal samples.

FIG. 10, includes another electrolyte (MEP Br) box 1012, used as described above in a testing (evaluation) operation "V" (diamond 1014), for a sample 1016, having an unknown metal content. Using the electrolyte and testing operations described herein, the unidentified sample 1016 causes a millivolt potential of 1702+/−15 mV to be generated. This voltage potential is then correlated to previously empirically identified voltages corresponding to characteristics of certain metal compositions (i.e., 6061 (Al/mG)).

FIG. 10 also shows the use of multiple probes with different electrolytes testing the same unknown metal sample in order to more definitively define that unknown sample. More particularly, returning to step 1012, a probe having 2M MEB Br electrolyte, performs an evaluation at step (diamond) 1014 on an unknown sample 1017. Dependent upon the characteristics and/or composition of the unknown sample 1017, a voltage 1785±10 mV or 1855±19 mV is detected by probing operations. It is to be understood that these values are selected as examples only and that if sample 1017 had other metal characteristics still other voltages would be returned. Therefore, it is to be appreciated that while unidentified sample 1017 is shown once as a single box, the single box is intended to represent the possibility of different metallic sample compositions for the purposes of this discussion. With this understanding, this example explanation will be continued. So when the voltage 1855±17 mV (dotted line) is detected, a preliminary identification has occurred (Aluminum Alloy 5086), but the user may wish to verify this identification. Therefore, a next step is to further probe check this sample (check value box) 1018 using an electrolyte of 2M FeCl$_3$+0.1M HCl. Then, as further testing is again done on that sample 1017 at evaluation step (diamond) 1020 and a voltage of 1500±4 mV is determined, this voltage is correlated with a known metal composition, i.e., 5086 (Al/Mg). In other words, box 1022 has verified the preliminary sample identification of box 1017.

The second part of this discussion (i.e., dealing with the voltage 1785±10 mV) returned by testing sample 1017 results in a failure to identify a particular metal composition. Then, similar to the previous discussion, a further probing operation is undertaken using the electrolyte 2M FeCl$_3$+0.1M HCl of box 1018 as used in an evaluation operation (diamond) 1020. In this situation, if the sample in box 1017 returns a voltage of 1499±4 mV, then it is correlated to 5052 (Al/Mg) as shown in box 1024. Similarly, if the evaluation returns a voltage of 1472±13 mV, it can be determined that the sample 1017 is the aluminum metal 1100 (Al) of box 1026.

The foregoing discussion is intended to show that a single sample may be tested by more than one probe, having different electrolytes. This multi-probing process narrows down the possibilities to more specifically identify an unknown metallic sample.

Still further FIG. 10 includes electrolyte (2M CoCl$_2$+HCl) box 1028, used in a testing operation "V" (diamond 1030), for an unknown sample 1032. The results of the testing operation results in a millivolt potential measurement of 1373+/−5 mV, for the metal sample 1032. This voltage value is then found to correlate to a specific metal—3003 (Al/Mn). FIG. 10 further shows other Al alloys may also be tested for by use of an appropriate electrolyte (boxes 1034, 1036).

The forgoing examples have described electrical excitation and measurement devices, 310, 810 as a single unit diagram. It is to be understood these functions maybe accomplished by separate device such as a signal generator, a voltmeter and ammeter, among other appropriate electronic devices.

Figure 11:
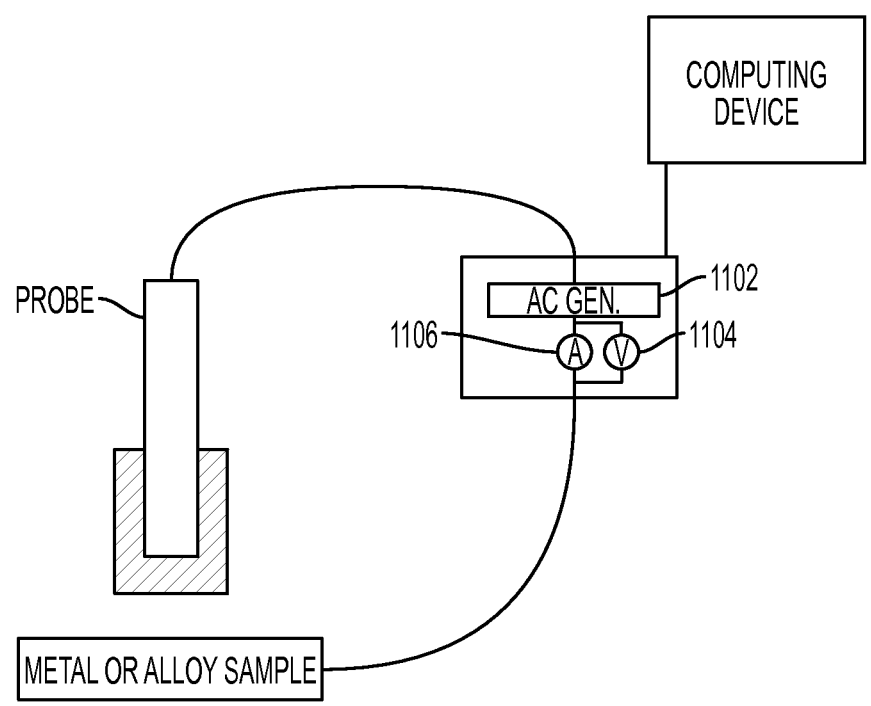
FIG. 11 provides a more detailed view of the electrical excitation and measurement device described in FIGS. 3 and 8.

Turning more particularly to FIG. 11, a more detailed view of the electrical excitation and measurement devices (302, 802) of the present disclosure (as shown in FIGS. 3 and 8) is provided. In one embodiment the electrical excitation and measurement device (302, 802), may consist of a AC current generator 1102, a voltmeter 1104, and an ammeter 1106. The output of the voltmeter 1104 and/or the ammeter 1106 being provided to the computing device (318, 818 of FIGS. 3 and 8 respectively).

Figure 12:
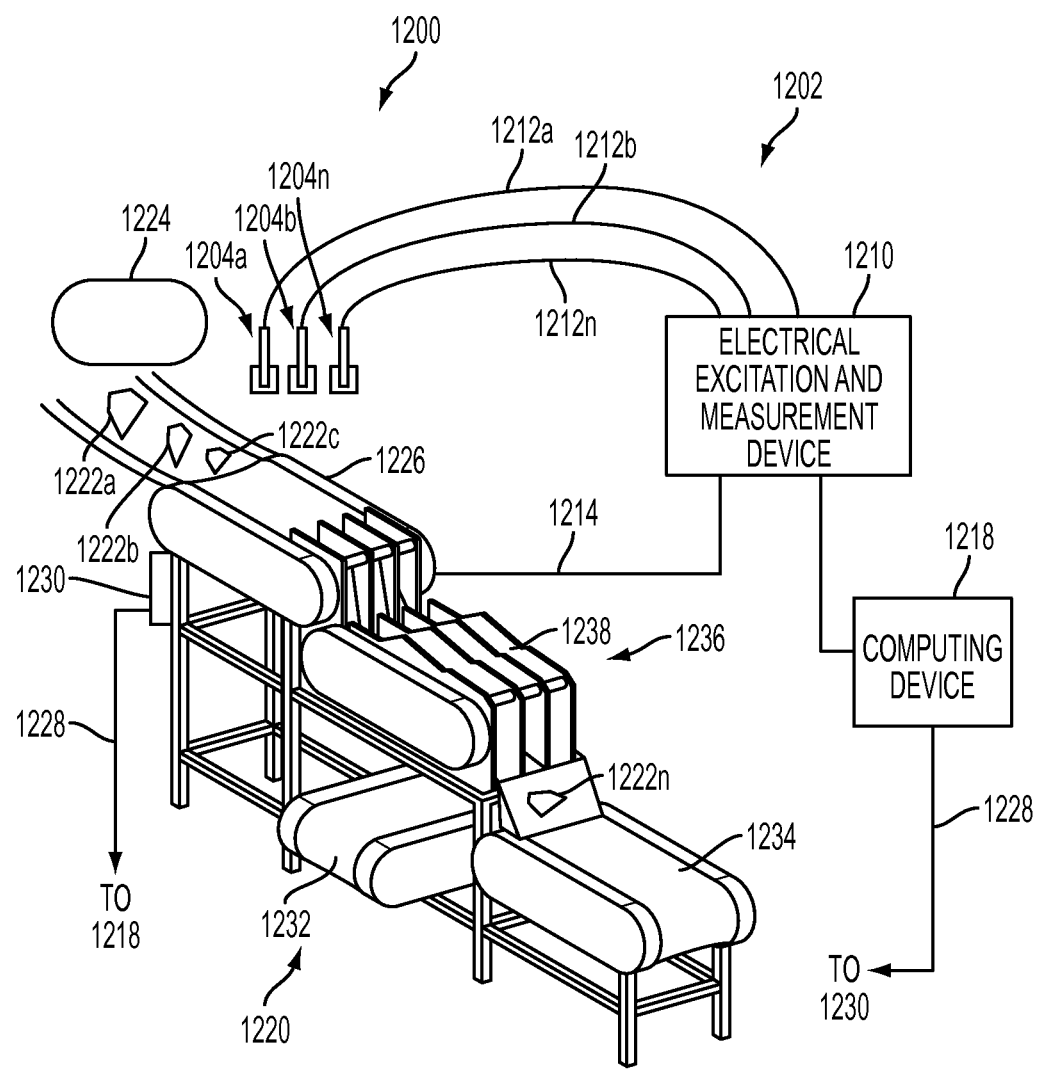
FIG. 12 illustrates the present concepts employed in connection with a conveyer system.

Turning to FIG. 12, illustrated is metallic sample identification system 1200 including a probe based electrochemical testing system 1202, such as has been previously described, in connection with FIGS. 3 and 8. The system 1202 includes metal probe arrangements 1204a, 1204b and 1204n, electrical excitation and measurement device 1210, electrical connectors 1212a, 1212b, 1212n and 1214, and computing device 1218. The electrochemical probing system 1202 is now shown in association with a conveyor system 1220 on which are metal samples 1222a, 1222b, 1222c and 1222n. System 1200 of FIG. 12 also includes a cleaning arrangement 1224, wherein the metal samples may be cleaned prior to be being probed by the probing system 1202.

It is known that in many situations, the metal or alloy sample being interrogated or tested may have dirt, paint or oxidation on its surface. Before the probes are used, the sample surface can be cleaned. The cleaning may be done in one or more of the following ways by an appropriately employed treatment system, as represented by system 1224:

I. A milling arrangement for milling a small portion of the sample surface.

II. An abrading arrangement for abrading the sample surface with a metal brush or with electro-chemically non-active sand-paper—such as Tungsten carbide papers.

II. A chemical cleaning arrangement for chemically cleaning the sample surface of the metal, such as with phosphoric acid.

It is to be noted that in testing system 1212, the probe arrangements 1204a-1204n are located near a first level 1226 of the conveyor system 1220. The probes may be arranged in such a way as to be controlled to be brought into contact with the metal samples as they are passing, such that testing is an ongoing rapid testing process. The conveyer system 1220 includes a controlled power system, such as a single or multiple motors to move the conveyor belts at a predetermined speed, where this speed is synchronized with the operational capabilities of the test system 1202. It is to be appreciated that while the probes are shown associated with the first level conveyor 1226, probes may be located at different locations of the conveyor system and are shown at the first level 1226 simply for convenience. Also, in one embodiment the electrical connector 1214 is electrically associated with the first conveyor system by a "streetcar" type connection. By streetcar connection it is meant that it is held in contact with the conveyor belt such that an electrical connection is maintained as the conveyor belt moves. It is of course to be appreciated that other electrical connections may be used.

Thus, in this system metallic samples (e.g., scrap metal) are carried on the conveyer belt system 1220. Then the probes (with electrolytes) are brought into operational contact with various ones of the metallic samples, resulting in a voltage potential generated not by connecting to the directly (e.g., metal to metal) but through the electrolyte. However, the electrical connection of electrical connector 1224 provides a metal-to-metal connection between the metallic samples 1222a-1222n and the conveyor belt (for example, upper level portion 1226), where no electrical potential results. Therefore the measurements being made by the testing system 1202 are not affected by the metal to metal connection (i.e., metal samples and metal conveyor belt) in determining the identification of the particular unknown samples on the conveyer belt system 1220.

Another aspect of the present disclosure has computing device 1218 in communication with conveyor system 1220, via line 1228, which is in operative connection with a controller/motor component 1230. In one embodiment once computing device 1218 has operated to correlate data readings (e.g., voltage values) from electrical excitation measurement device 1210, to identify the type of metal or metal alloy of a particular sample, the computing device outputs this information to controller/motor component 1230, which in turn sorts the identified sample to a particular area of the conveyor system. For example, the movement of the metal or metal alloy causes the identified sample to be processed to either lower conveyor system portion 1232 or 1234, by movement of redirector mechanisms 1236 of middle conveyer system portion 1238 controlled by controller/motor component 1230.

Having disclosed various details of the present concepts, the following summarizes and provides additional disclosure. Particularly, the preceding discussion disclosed an electrochemical probe based testing system for identification of the content of metallic samples. The testing system includes, at least one electrically conductive probe, at least one electrically non-conductive membrane carrying an electrolyte and being in operative connection with the at least one electrically conductive probe. Also provided in the testing system are separate electrical connections to each of the at least one electrically conductive probe and an electrical connection to the metallic sample being tested. The at least one electrically conductive probe is positioned against the metallic sample with the at least one electrically non-conductive membrane located in between, establishing an ionic path between each of the electrically conductive probes and the metallic sample(s). An electrical excitation device of the test system provides, to each of the electrically conductive probes, asymmetric excitations to the electrically conductive probe. Also part of the test system is an electrical measurement device to measure at least one of voltages and currents between the probe and the metallic sample, and an electronic computing device configured to operate an algorithm and/or store a look-up table that correlates the measured voltages with respective previously stored characteristic voltage values, to identify metal and/or alloy compositions of the metallic sample being tested.

In various implementations, the electrically conductive probe of the test system is made out of glassy carbon, graphite, carbon-plastic composite, other forms of carbon, as well as metal that forms a galvanic coupling through the electrolyte with the metallic sample, a metal salt or metal salt composite (such as Tin, Lead, Indium) that form a galvanic coupling through the electrolyte with the metallic sample material. The probe may also be made out of metal oxide or chalcogenide based materials.

In certain embodiments the membrane is a porous or fibrous polymeric material with open pores, and is in at least one of a planar form or shaped as a sleeve that covers the probe. It is further noted the membrane is at times configured to be re-used for multiple measurements, or discarded after each measurement. On other embodiments the membrane is a non-porous ion exchange membrane.

In certain embodiments the electrolyte is capable of exchanging a reversible redox reaction with the metals present in the metallic sample being probed. A cation of the electrolyte consists of a metal ion having at least two redox states that are soluble in the electrolyte medium. Certain appropriate metal redox cations include but are not limited to, $Fe^{2+}/Fe^{3+}$, $Ce^{3+}/Ce^{4+}$, $V^{2+}/V^{3+}$, $V^{3+}/V^{4+}$, $V^{4+}/V^{5+}$, $Cu^+/Cu^{2+}$, and $Sn^{2+}/Sn^{4+}$, $Ni^{2+}/Ni^{3+}$.

In certain embodiments the probe based test system includes a cleaning arrangement or configuration to clean a surface of the metallic sample prior to the membrane being positioned in operative association with the probe to make operational contact with the metallic sample being tested. The cleaning configuration including at least one of an abrasive cleaning arrangement, a chemical cleaning arrangement, a milling based cleaning arrangement, a chemical etch cleaning arrangement, and a mechanical puncture based cleaning arrangement.

In certain embodiments excitations of the electrical excitation device includes alternating current with a current density having any value between and including approximately $0.1\ uA/cm^2$ to $10\ mA/cm^2$, where the alternating current is asymmetric in magnitude, and the electronic excitation device which generates the asymmetric alternating current is programmed such that the net electronic charge transferred between the probe and the sample is zero.

In certain embodiments where the net electrical excitation to the sample is null, the measurement taken by the electronic measurement device is a voltage measurement (e.g., open circuit voltage)

In certain embodiments the electrical excitation to the sample is an applied and positive constant current of between approximately $0.1\ uA/cm^2$ and $10\ mA/cm^2$, and a negative constant current of between approximately $0.1\ uA/cm^2$ and $10\ mA/cm^2$.

In the present application the test system is employed in a method for electrochemically identifying a metallic sample. This method includes establishing an ionic path between an electrically conductive probe and a metallic sample by placement of an electrically non-conductive membrane embedded with or soaked in an electrolyte, between and in contact with the electrically conductive probe and the metallic sample.

The method then generates and provides current asymmetric excitations to the electrically conductive probe and the metallic sample. Thereafter the method measures voltages between the probe and sample, by use of an electronic measuring device, and the measured voltages are correlated with voltages characteristic and/or corresponding to respective metal and/or metal alloy compositions to identify the metallic sample as having a specific metal or metal alloy.

An alternative to the previously described probe based testing system, includes an electrochemical probe system for identification of a metallic sample, which includes an electrically conductive probe, an electrically non-conductive component in operative association with the electrically conductive probe, an electrolyte carried by the electrically non-conductive component, and an electrical connection to the electrically conductive probe. The system further includes an electrical connection to the metallic sample, wherein, an ionic path is formed with the electrically conductive probe positioned against the metallic sample with the electrically non-conductive component located there between. Also provided is an electrical excitation device configured to provide asymmetric current pulses to the electrically conductive probe, and an electrical measurement device to measure voltage potentials between the electrically conductive probe and the metal sample under test. Finally, an electronic computing device is configured to store voltage values representing various metals and/or metal alloys. The electronic computing device stores the representative voltage values, and receives the measured voltages from the electronic measurement device. Using this data the electronic computing device operates to correlate the measured voltages with the stored voltages to identify respective metal and/or metal alloy compositions of the metallic sample under test.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. An electrochemical probe system for identification of a metallic sample, comprising:
   a first electrically conductive probe;
   a first electrically non-conductive component carrying a first electrolyte and being in operative connection with the first electrically conductive probe;
   a second electrically conductive probe;
   a second electrically non-conductive component carrying a second electrolyte different from the first electrolyte, and being in operative connection with the second electrically conductive probe;
   a separate electrical connection to at least one of the first electrically conductive probe and the second electrically conductive probe;
   an electrical connection to the metallic sample, wherein the first electrically conductive probe is positioned against the metallic sample with the first electrically non-conductive component located in between, establishing an ionic path between the first electrically conductive probe and the metallic sample;
   another electrical connection to the metallic sample, wherein the second electrically conductive probe is positioned against the metallic sample with the second electrically non-conductive component located in between, establishing an ionic path between the second electrically conductive probe and the metallic sample;
   an electrical excitation device to provide to the first electrically conductive probe, the second electrically conductive probe and the metallic sample, asymmetric excitations;
   an electrical measurement device to measure at least one of voltages and currents between the first electrically conductive probe and the metallic sample, and between the second electrically conductive probe and the metallic sample; and
   an electronic computing device configured to operate an algorithm and/or store a look-up table that correlates the at least one of measured currents and voltages with respective metal and/or alloy compositions of the metallic sample, the metallic sample including one or more pieces of metal and/or metal alloy, wherein the second electrically conductive probe and the second electrically non-conductive component carrying the second electrolyte assist in obtaining additional correlations in addition to those correlations associated with the first electrically conductive probe and the first electrically non-conductive component carrying the first electrolyte.

2. The probe system of claim 1, wherein the first and second electrically conductive probes are each made out of at least one of glassy carbon, graphite, carbon-plastic composite, and other forms of carbon.

3. The probe system of claim 1, wherein the first and second electrically conductive probes are made out of a metal that forms a galvanic coupling through the first and second electrolytes with the metallic sample.

4. The probe system of claim 1, wherein the first and second electrically conductive probes are each made out of a metal salt or metal salt composite that forms a galvanic coupling through the first and second electrolytes with the metallic sample.

5. The probe system of claim 1, wherein each of the first and second electrically non-conductive components are configured as membranes composed of a porous or fibrous polymeric material with open pores, and wherein the membranes are in at least one of a planar format and shaped as a sleeve that covers the probe, and wherein the membrane is configured to be re-used for multiple measurements, or discarded after each measurement.

6. The probe system of claim 1, wherein each of the first and second electrically non-conductive components include a non-porous ion exchange membrane.

7. The probe system of claim 1, wherein the first and second electrolytes are capable of exchanging a reversible redox reaction with the metals present in the metallic sample being probed.

8. The electrolyte of claim 7, wherein a cation consists of a metal ion having at least two redox states that are soluble in the first and second electrolyte medium.

9. The electrolyte of claim 7, wherein metal redox cations are one of $Fe^{2+}/Fe^{3+}$, $Ce^{3+}/Ce^{4+}$, $V^{2+}/V^{3+}$, $V^{3+}/V^{4+}$, $V^{4+}/V^{5+}$, $Cu^{+}/Cu^{2+}$, $Sn^{2+}/Sn^{4+}$, $Ni^{2+}/Ni^{3+}$.

10. The probe system of claim 1, further including a cleaning arrangement to clean a surface of the metallic sample, the cleaning arrangement including at least one of an abrasive cleaning arrangement, a chemical cleaning arrangement, a milling based cleaning arrangement, a chemical etching cleaning arrangement, and a mechanical puncture based cleaning arrangement.

11. The probe system of claim 1, wherein the excitations of the electrical excitation device includes alternating current with a current density having any value between and including approximately 0.1 uA/cm2 to 10 mA/cm2.

12. The probe system of claim 1, wherein a net electrical excitation to the metallic sample is null, and the measurement taken is a voltage measurement.

13. The probe system of claim 1, wherein the electrical excitation to the metallic sample is an applied and positive constant current of between, approximately 0.1 uA/cm2 and 10 mA/cm2.

14. The probe system of claim 1, wherein the electrical excitation to the metallic sample is an applied and negative constant current of between, approximately −0.1 uA/cm2 and −10 mA/cm2.

15. A method for electrochemically identifying a metallic sample, comprising:
- establishing a first ionic path between a first electrically conductive probe and a metallic sample by placement of a first electrically non-conductive membrane carrying a first electrolyte, between and in operative contact with the first electrically conductive probe and the metallic sample;
- establishing a second ionic path between a second electrically conductive probe and a metallic sample by placement of a second electrically non-conductive membrane carrying an electrolyte, between and in operative contact with the second electrically conductive probe and the metallic sample;
- generating and providing asymmetric excitations to the electrically conductive probe and the metallic sample;
- measuring at least one of voltages and currents between the first and second probes and the metallic sample, by use of an electronic measuring device; and
- correlating the measured voltages and currents of the first and second probes with voltages and currents corresponding to respective metal and/or metal alloy compositions to identify the metallic sample as including a specific metal and/or metal alloy, the metallic sample including one or more pieces of metal and/or metal alloy.

16. An electrochemical probe system for identification of a metallic sample comprising:
- a first electrically conductive probe;
- a first electrically non-conductive component in operative association with the first electrically conductive probe;
- a second electrically conductive probe;
- a second electrically non-conductive component in operative association with the second electrically conductive probe;
- an electrolyte carried by the first and second electrically non-conductive component;
- a separate electrical connection to each of the first electrically conductive probe and the second electrically conductive probe;
- an electrical connection to the metallic sample including the first electrically conductive probe, and the first electrically non-conductive component;
- another electrical connection to the metallic sample including the first electrically conductive probe, and the first electrically non-conductive component;
- wherein, an ionic path is formed with the first and second electrically conductive probes positioned against the metallic sample with the respective electrically first and second non-conductive components located there between;
- an electrical excitation device configured to provide asymmetric current pulses to the electrically conductive probes and the metallic sample;
- an electrical measurement device to measure voltage potentials and currents between the electrically conductive probes and the metallic sample; and
- an electronic computing device configured to operate an algorithm and/or store voltages and currents representing various metals and/or metal alloys, to receive the measured voltages and currents from the electronic measurement device and to correlate the measured voltages and currents with the stored voltages and currents to identify respective metal and/or metal alloy compositions of the metallic sample, wherein the metallic sample includes one or more pieces of metal and/or metal alloy.

17. An electrochemical probe system for identification of a metallic sample, comprising:
- at least one electrically conductive probe;
- at least one electrically non-conductive component carrying an electrolyte and being in operative connection with the at least one electrically conductive probe;
- a separate electrical connection to each at least one electrically conductive probe;
- an electrical connection to the metallic sample, wherein the at least one electrically conductive probe is positioned against the metallic sample with the at least one electrically non-conductive component located in between, establishing an ionic path between each of at least one electrically conductive probe and the metallic sample;
- an electrical excitation device to provide to each at least one electrically conductive probe and the metallic sample, asymmetric excitations, wherein the excitations of the electrical excitation device includes alternating current with a current density having any value between and including approximately 0.1 uA/cm2 to 10 mA/cm2;
- an electrical measurement device to measure at least one of voltages and currents between the probe and the metallic sample; and
- an electronic computing device configured to operate an algorithm and/or store a look-up table that correlates the measured currents and voltages with respective metal and/or alloy compositions of the metallic sample, wherein the metallic sample includes one or more pieces of metal and/or metallic alloy.

18. The probe system of claim 17, wherein the alternating current is asymmetric in magnitude.

19. The probe system of claim 17, wherein the electronic excitation device which generates the asymmetric alternating current is programmed such that the net electronic charge transferred between the probes and the sample is zero.

* * * * *